United States Patent [19]
Mynderse et al.

[11] Patent Number: 5,202,242
[45] Date of Patent: Apr. 13, 1993

[54] A83543 COMPOUNDS AND PROCESSES FOR PRODUCTION THEREOF

[75] Inventors: Jon S. Mynderse, Indianapolis; James W. Martin, Coatesville; Jan R. Turner, Carmel; Lawrence C. Creemer, Indianapolis; Herbert A. Kirst, Indianapolis; Mary C. Broughton, Indianapolis; Mary L. B. Huber, Danville, all of Ind.

[73] Assignee: DowElanco, Indianapolis, Ind.

[21] Appl. No.: 790,287

[22] Filed: Nov. 8, 1991

[51] Int. Cl.$^5$ .................. C12P 19/62; C12P 19/60; C12R 1/01
[52] U.S. Cl. .................................. 435/76; 435/75; 435/822
[58] Field of Search .................. 435/75, 76, 822

[56] References Cited

U.S. PATENT DOCUMENTS

| | | | |
|---|---|---|---|
| 4,148,883 | 4/1979 | Celmer et al. | 424/122 |
| 4,206,206 | 6/1980 | Mori et al. | 435/82 |
| 4,224,314 | 9/1980 | Celmer et al. | 435/171 |
| 4,261,511 | 2/1981 | Whaley et al. | 435/169 |
| 4,293,651 | 10/1981 | Whaley et al. | 435/822 |
| 4,321,329 | 3/1982 | Whaley et al. | 435/253 |
| 4,448,970 | 5/1984 | Magerlein | 548/336 |
| 4,501,752 | 2/1985 | Yokoi et al. | 514/414 |
| 4,515,942 | 5/1985 | Iwasaki et al. | 536/16.8 |

FOREIGN PATENT DOCUMENTS

| | | |
|---|---|---|
| 375316 | 12/1989 | European Pat. Off. |
| 46-028833 | 8/1971 | Japan . |
| 48-039922 | 12/1973 | Japan . |
| 55000310 | 1/1980 | Japan . |
| 59-151896 | 8/1984 | Japan . |
| 59-170092 | 9/1984 | Japan . |
| 60-160888 | 8/1985 | Japan . |
| 85053597 | 11/1985 | Japan . |
| 62-226925 | 10/1987 | Japan . |
| 63-045280 | 2/1988 | Japan . |

OTHER PUBLICATIONS

Kirst et al., Tetrahedon Leters (1991), 32(37):4839–4842.
Whaley et al., Tetrahedron ltr. (1980), 21:3659.
Kreuzman et al., J. Biological Chemistry (1988), 263(30):15626–15633.
Snyder et al., J. Am. Chem. Soc., (1984) 106:787.
Mertz and Yao, Int'l J of Systematic Bacteriology (1990), 40(1):34–39.
Celmer et al., J. Chem. Soc. (1980) 102:4203.
Borchardt et al. (1979), Biochem. & Biophys. Res. Comm., 89(3):919–924.
Vedel et al., (1978), Biochem. & Biophys. Res. Comm., 85(1):371–376.
Pickett, J. A., (1988), Chemistry in Britain, 137–142.
Omura, (1984), Macrolide Antibiotics, Chapter 13.
Fuller (1978), Biochemical Pharmacology, 27:1981–1983.
Jackson et al. (1988), Abstracts of the 1988 ICAAC, 26026.
Umezawa (1980), The Journal of Antibiotics, 33(3):15–26.

(List continued on next page.)

*Primary Examiner*—Herbert J. Lilling
*Attorney, Agent, or Firm*—James P. Leeds; Thomas D. Zindrick; Kenneth L. Loertscher

[57] ABSTRACT

New fermentation products A83543L, A83543M, and A83543N, N demethyl derivatives thereof, and salts thereof, are useful for the control of insects. A83543-PsaL1 is useful for the preparation of A83543 components. Methods for making A83543J, A83543L, A83543M, and A83543N by culture of *Saccharopolyspora spinosa* NRRL 18719 or NRRL 18720 are provided. Insecticidal and ectoparasiticidal compositions containing A83543L, A83543M, A83543N, and N-demethyl derivatives thereof are also provided.

7 Claims, 7 Drawing Sheets

OTHER PUBLICATIONS

Umezawa, Index of Antibiotics from Actinomycetes, vol. 2.
Omura and Tannaka (1984), Macrolide Antibiotics, Chapter 1 pp. 3 and 9.
Schulman and Ruby (1987), Antimicrobial Agents and Chemotherapy, 31(6):964–965.
Schulman et al (1985), The Journal of Antibiotics, 1494–1498.
Ito and Hirata (1972), Tetrahedron Letters, 12:1185–1188.
Aizawa et al. (1979), The Journal of Antibiotics, 22(3):193–196.
Ikeda, et al. (1985), J. Antibiotic, 38:436.
Jomon et al., (1972), The Journal of Antibiotics, 25(5):271–280.
Dybas and Babu (1988), Brighton Crop Protection Conference, 57–64.
Aizawa et al. (1979), J. Antibiot., 32:193.
Ito et al. (1972), Tetrahedron Letters, 11.81, 1185, 2557.
Aizawa et al., (1979), J. Antibiot., 32:193.
Derwent Abstract 84-278337/45, SSSE 16.03.83.
Derwent Abstract 84-252941/41, SSSE 16.02.83.
Derwent Abstract 92:144960k.
Derwent Abstract 11667c/07, KAKE 31.05.78.
Derwent Abstract 92:211459u.
Derwent Abstract 88-095030/14, SSSE 00.00.86.
Derwent Abstract 85-245719/40, SSSE 01.02.84.
Derwent Abstract 54333S-BCD, Fuji, 17.02.69.
Derwent Abstract 80-11667C/07.
Catalogue of bacteria and phages, ATTCC, 7th Ed., 1989.

A83543 COMPOUNDS AND PROCESSES FOR PRODUCTION THEREOF

BACKGROUND OF THE INVENTION

Target insects are rapidly developing resistance to the insecticides which are presently available. Resistance to insecticides in arthropods is widespread, with at least 400 species exhibiting resistance to one or more insecticides. The development of resistance to older insecticides, such as DDT, the carbamates, and the organophosphates, is well documented. See Brattsten, Holyoke, Leeper, and Raffa, "Insecticide Resistance: Challenge to Pest Management and Basic Research," *Science*, 231, 1255 (1986). Resistance to synthetic insecticides has developed extremely rapidly, including the development of resistance to the newer pyrethroid insecticides. Pickett, "Chemical Pest Control—the New Philosophy, *Chem. Britain*, 137 (1988). Therefore, new insecticides are in demand.

Fermentation product A83543, a family of related factors produced by *Saccharopolyspora spinosa*, was recently discovered and was shown to exhibit excellent insecticidal activity. Previously, fermentation product A83543 was shown to comprise individual components A83543A, A83543B, A83543C, A83543D, A83543E, A83543F, A83543G, A83543H, and A83543J. European Patent Publication No. 0 375 316. The general structure was shown to consist of a 5,6,5-tricyclic ring system fused to a 12-membered macrocyclic lactone, a neutral sugar, and an amino sugar. Kirst et al., *Tetrahedron Letters*, 32, 4839 (1991). European Patent Application No. 0 375 316 A1 also discloses six pseudoaglycones, A83543PsaA1, A83543PsaD1, A83543PsaE1, A83543PsaF1, A83543PsaH1, and A83543PsaJ1, which are produced by removing the amino sugar from A83543A, A83543D, A83543E, A83543F, A83543H, and A83543J, respectively. Removing the amino sugar from factor A83543B, A83543C, or A83543G also produces A83543PsaA1.
A83543PsaA1.

The following table identifies by structure these known A83543 compounds.

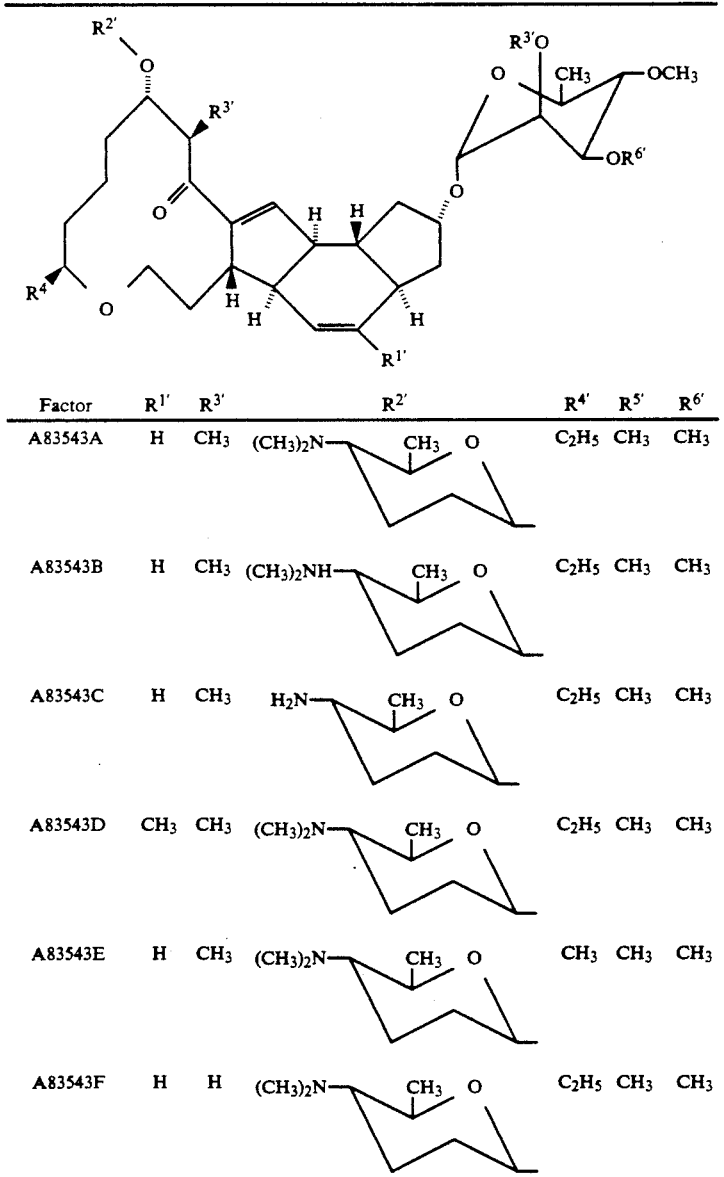

| Factor | $R^{1'}$ | $R^{3'}$ | $R^{2'}$ | $R^{4'}$ | $R^{5'}$ | $R^{6'}$ |
|---|---|---|---|---|---|---|
| A83543A | H | $CH_3$ | $(CH_3)_2N$— | $C_2H_5$ | $CH_3$ | $CH_3$ |
| A83543B | H | $CH_3$ | $(CH_3)_2NH$— | $C_2H_5$ | $CH_3$ | $CH_3$ |
| A83543C | H | $CH_3$ | $H_2N$— | $C_2H_5$ | $CH_3$ | $CH_3$ |
| A83543D | $CH_3$ | $CH_3$ | $(CH_3)_2N$— | $C_2H_5$ | $CH_3$ | $CH_3$ |
| A83543E | H | $CH_3$ | $(CH_3)_2N$— | $CH_3$ | $CH_3$ | $CH_3$ |
| A83543F | H | H | $(CH_3)_2N$— | $C_2H_5$ | $CH_3$ | $CH_3$ |

-continued

| Factor | R1' | R3' | R2' | R4' | R5' | R6' |
|---|---|---|---|---|---|---|
| A83543G | H | $CH_3$ | (CH$_3$)$_2$N-[sugar]-$CH_3$ | $C_2H_5$ | $CH_3$ | $CH_3$ |
| A83543H | H | $CH_3$ | (CH$_3$)$_2$N-[sugar with $CH_3$, O] | $C_2H_5$ | H | $CH_3$ |
| A83543J | H | $CH_3$ | (CH$_3$)$_2$N-[sugar with $CH_3$, O] | $C_2H_5$ | $CH_3$ | H |
| A83543PsaA1 | H | $CH_3$ | H | $C_2H_5$ | $CH_3$ | $CH_3$ |
| A83543PsaD1 | $CH_3$ | $CH_3$ | H | $C_2H_5$ | $CH_3$ | $CH_3$ |
| A83543PsaE1 | H | $CH_3$ | H | $CH_3$ | $CH_3$ | $CH_3$ |
| A83543PsaF1 | H | H | H | $C_2H_5$ | $CH_3$ | $CH_3$ |
| A83543PsaH1 | H | $CH_3$ | H | $C_2H_5$ | H | $CH_3$ |
| A83543PsaJ1 | H | $CH_3$ | H | $C_2H_5$ | $CH_3$ | H |

Of the known A83543 compounds, A83543J and A83543PsaJ1 are 3'-O-desmethyl compounds, i.e. compounds wherein $R^{6'}$ is H.

As used herein, the term "A83543 component" means a compound selected from the group consisting of A83543A, A83543B, A83543C, A83543D, A83543E, A83543F, A83543G, A83543H and A83543J. A83543 and each of the components are useful for the control of mites and insects, particularly Lepidoptera and Diptera species.

SUMMARY OF THE INVENTION

This invention provides 3'-O-desmethyl A83543 compounds of the formula 1

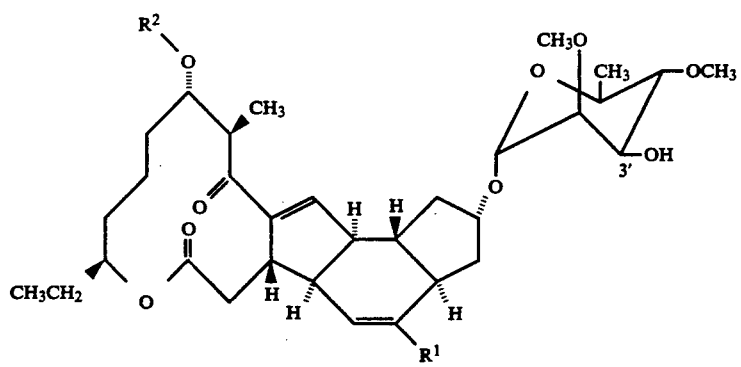

wherein R1 and R2 are selected from the following combinations of values:

| Compound | R¹ | R² |
|---|---|---|
| Compound 1 A83543L | CH₃ | (CH₃)₂N— (structure) |
| Compound 2 A83543M | H | (CH₃)₂NH— (structure) |
| Compound 3 A83543N | CH₃ | (CH₃)₂NH— (structure) |
| Compound 4 | H | H₂N— (structure) |
| Compound 5 | CH₃ | H₂N— (structure) |
| Compound 6 A83543PsaL1 | CH₃ | H | or an acid addition salt thereof when $R^2$ is other than hydrogen.

In particular, this invention relates to new components of fermentation product A83543. The new components have been designated A83543L, A83543M, and A83543N. The term "new A83543 component" means a compound selected from the group consisting of A83543L, A83543M, and A83543N. The invention also provides two new compounds, compounds 4 and 5, that can be prepared by chemical demethylation of A83543M and A83543N, respectively. Further, the invention provides a new A83543 pseudoglycone, which has been designated A83543PsaL1.

Another aspect of this invention is a process for producing a 3'-O-desmethyl A83543 compounds of formula 2

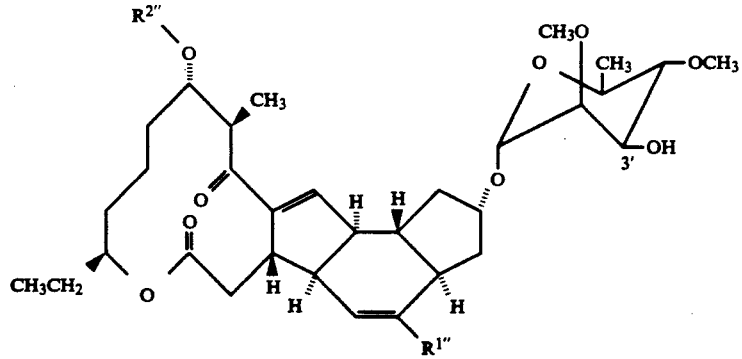

wherein $R^{1''}$ is hydrogen or methyl; and $R^{2''}$ is a group of formula

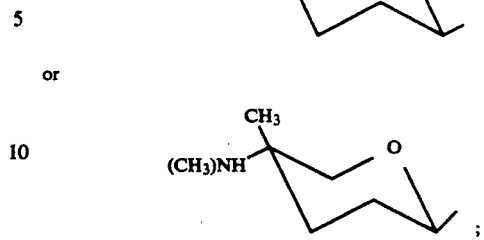

or (structure with (CH₃)NH)

;

which comprises culturing an A83543J producing strain of *Saccharopolyspora spinosa*, derived from culture A83543.1. Formula 2 encompasses A83543J, A83543L, A83543M, and A83543N.

Because *Saccharopolyspora spinosa* strains NRRL 18719 and NRRL 18720 are newly discovered strains, this invention further provides a biologically purified culture of these microorganisms.

The formula 1 compounds wherein $R^2$ is other than hydrogen are useful for the control of insects, particularly Lepidoptera, Homoptera, and Diptera species. Therefore, insecticidal compositions and methods for reducing the populations of insects using these compounds are also a part of this invention.

DETAILED DESCRIPTION OF THE INVENTION

The chemical structures of A83543L, A83543M, and A83543N were determined by spectrometric methods, including infrared spectroscopy (IR), nuclear magnetic resonance spectroscopy (NMR), and ultraviolet spectroscopy (UV), and by comparison to the known A83543 components. Kirst, Michel, Martin, Creemer, Chio, Yao, Nakatsukasa, Boeck, Occolowitz, Paschal, Deeter, Jones, and Thompson, *Tetrahedron Letters*, 32, 4839 (1991) and EPO Application No. 0 375 316. The following paragraphs describe the physical and spectral properties of A83543L, A83543M, and A83543N.

Characteristics of A83543L

Figure 1:
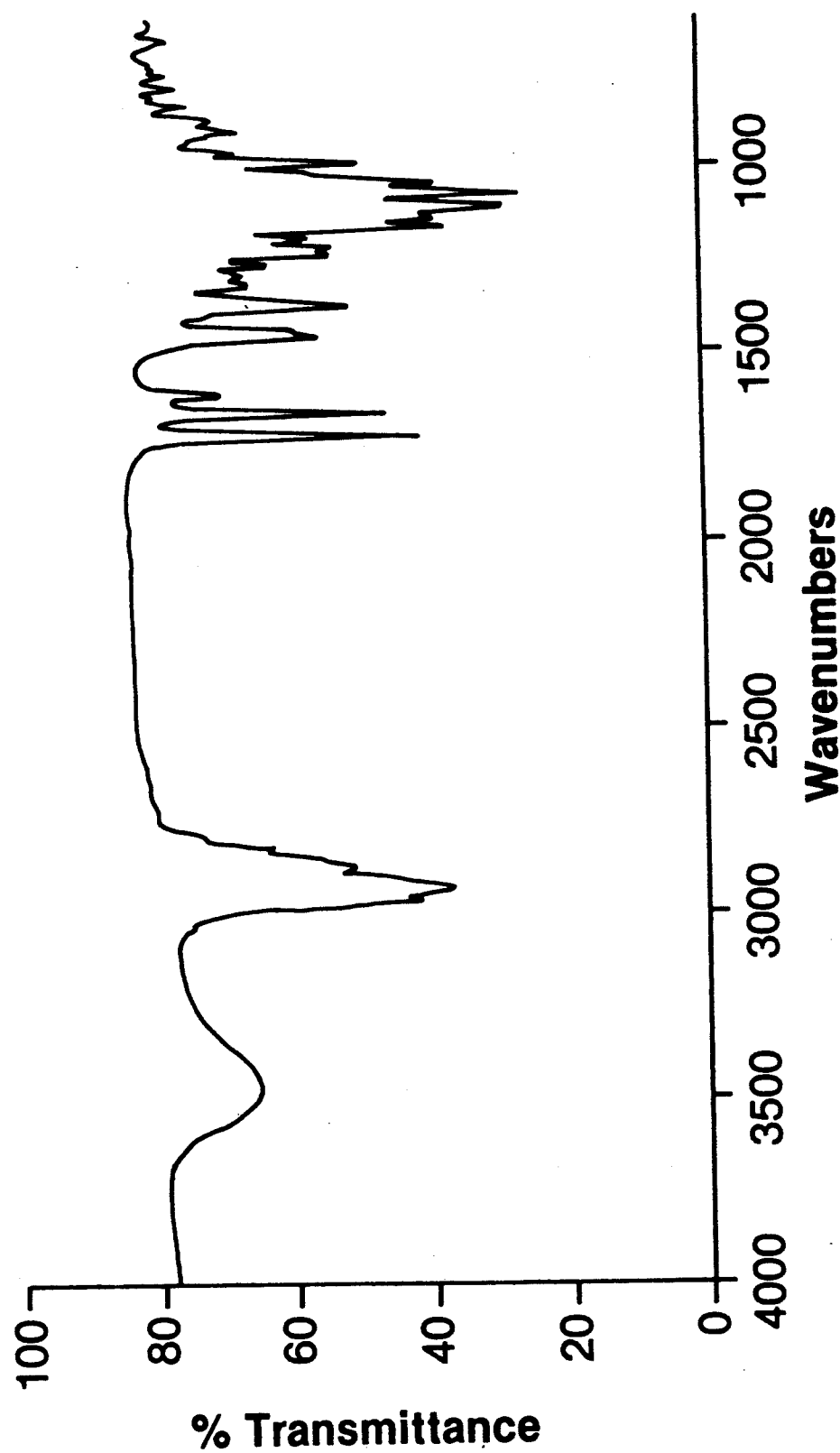
FIG. 1 shows the infrared absorption spectrum of A83543L in KBr.
Figure 2:
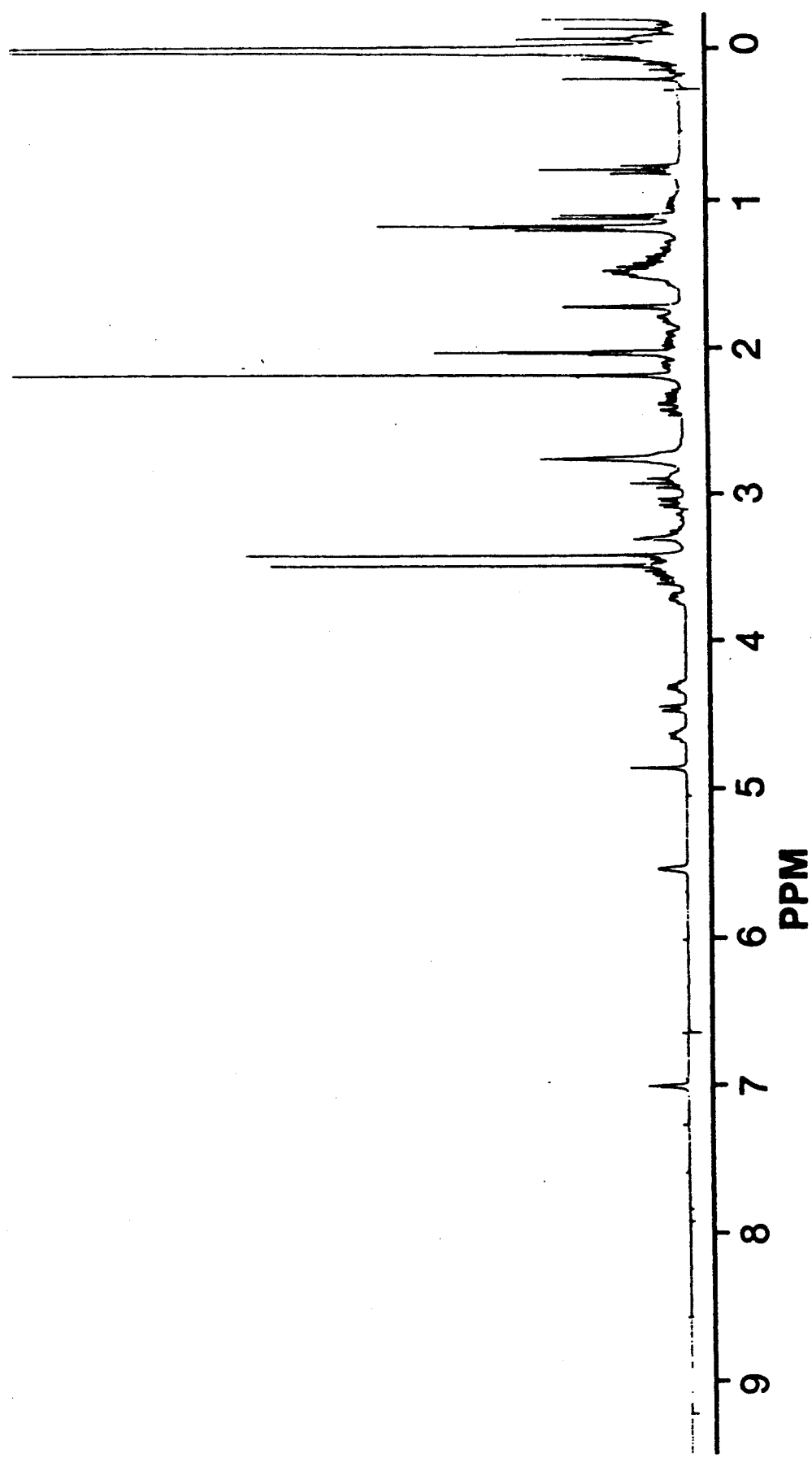
FIG. 2 shows the proton nuclear magnetic resonance spectrum (300 MHz) of A83543L in acetone-d₆.

A83543L has the following characteristics:
Molecular weight: 731
Empirical formula: $C_{41}H_{65}NO_{10}$
UV (EtOH): 244 nm ($\epsilon$10,362)
IR (KBr): see FIG. 1
MS (FAB): (M+H) m/z 732

Table I summarizes the $^1H$ and $^{13}C$ nuclear magnetic resonance (NMR) spectral data for A83453L (in acetone-$d_6$).

TABLE I $^1H$ and $^{13}C$ NMR data of A83543L in acetone-$d_6$

| Position | $^{13}C$ | $^1H$* |
|---|---|---|
| 1 | 172.59 | — |
| 2 | 34.32 | 3.07/2.42 |
| 3 | 48.39 | 2.91 |
| 4 | 42.75 | 3.45 |
| 5 | 123.29 | 5.53 |
| 6 | 137.19 | — |
| 7 | 45.33 | 2.18 |
| 8 | 35.61 | 2.01/1.45 |
| 9 | 76.62 | 4.32 |
| 10 | 38.59 | 2.36/1.38 |
| 11 | 46.99 | 1.03 |
| 12 | 49.99 | 2.77 |
| 13 | 148.51 | 7.02 |
| 14 | 145.11 | — |
| 15 | 203.09 | — |
| 16 | 48.43 | 3.30 |
| 17 | 80.91 | 3.55 |
| 18 | 35.04 | 1.55 |
| 19 | 22.50 | 1.79/1.19 |
| 20 | 30.89 | 1.53 |
| 21 | 76.81 | 4.45 |
| 22 | 29.11 | 1.49 |
| 23 | 9.55 | 0.81 |
| 24 | 16.29 | 1.13 |
| 6-$CH_3$ | 20.85 | 1.74 |
| 1' | 96.37 | 4.86 |
| 2' | 82.44 | 3.33 |
| 3' | 72.33 | 3.73 |
| 4' | 84.59 | 2.95 |
| 5' | 68.34 | 3.50 |
| 6' | 18.31 | 1.20 |
| 2'-$OCH_3$ | 59.05 | 3.44 |
| 4'-$OCH_3$ | 60.74 | 3.51 |
| 1" | 104.06 | 4.46 |
| 2" | 31.90 | 1.93/1.39 |
| 3" | 18.74 | 1.83/1.52 |
| 4" | 65.97 | 2.12 |
| 5" | 74.04 | 3.57 |
| 6" | 19.39 | 1.21 |
| $N(CH_3)_2$ | 40.97 | 2.21 |

*Shifts were taken from the $^1H$ spectrum or 2D $^1H/^{13}C$ one bond correlation.

Characteristics of A83543M

Figure 3:
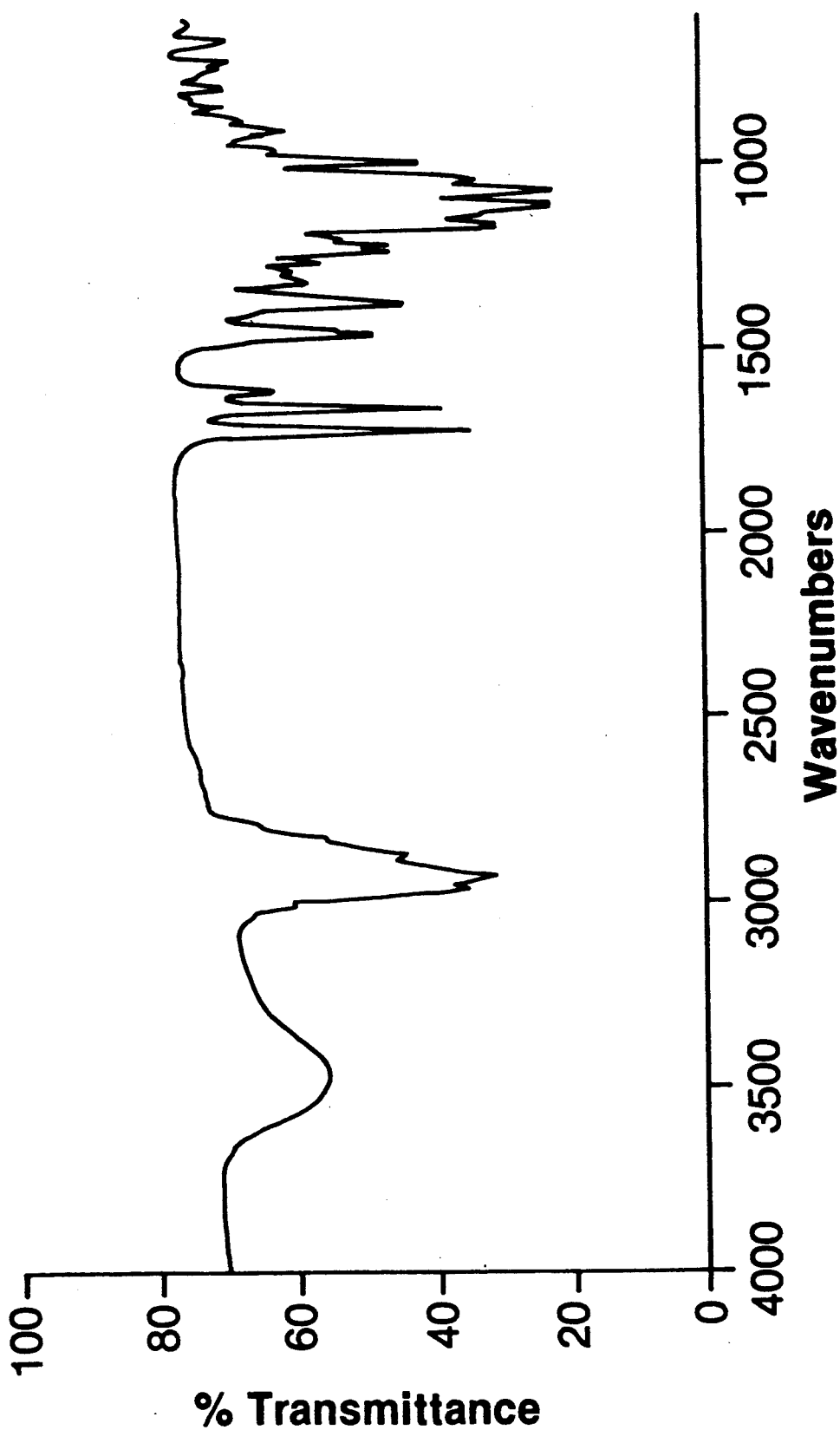
FIG. 3 shows the infrared absorption spectrum of A83543M in KBr.
Figure 4:
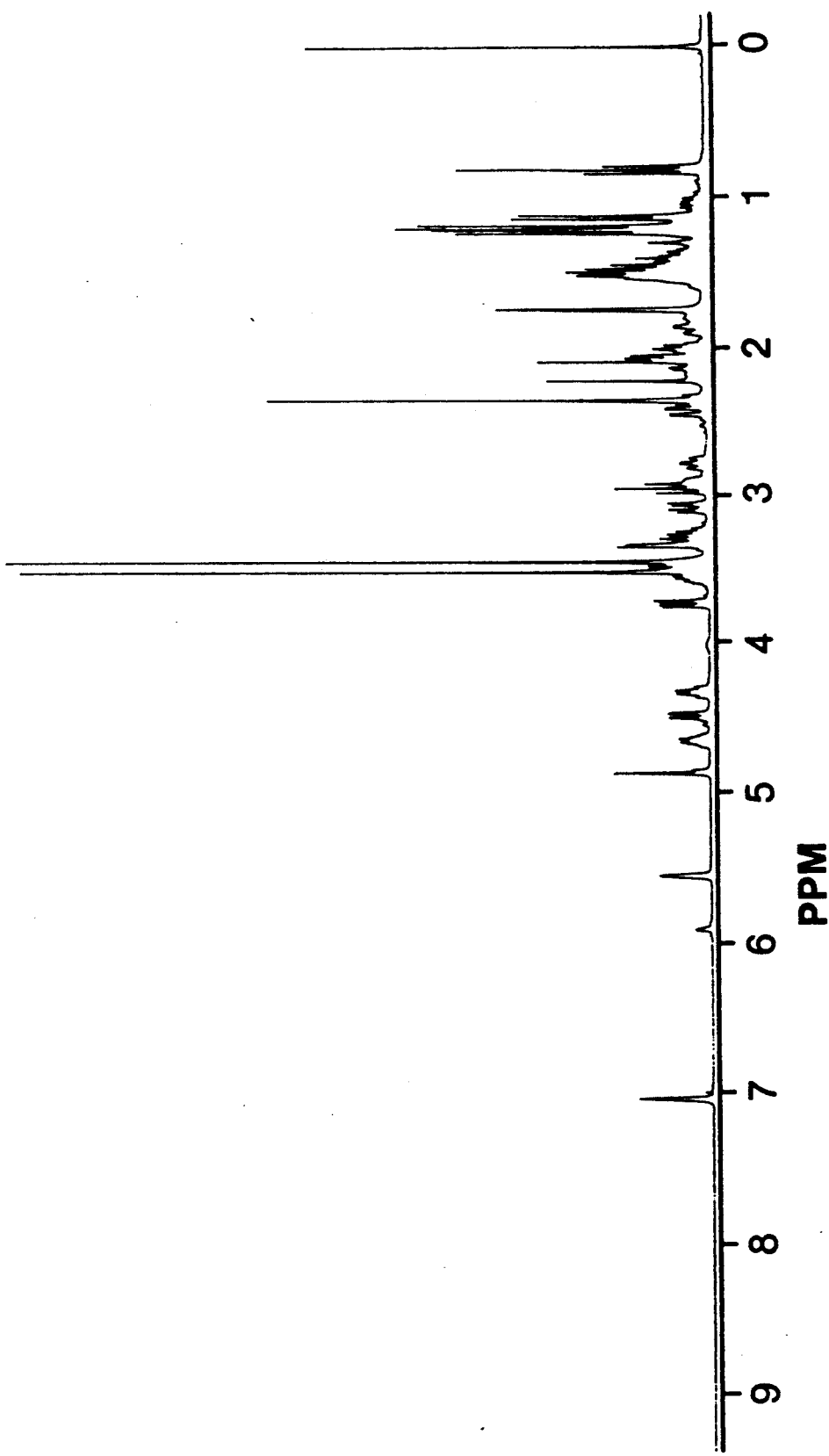
FIG. 4 shows the proton nuclear magnetic resonance spectrum (300 MHz) of A83543M in acetone-d₆.

A83543M has the following characteristics:
Molecular weight: 703
Empirical formula: $C_{39}H_{61}NO_{10}$
UV (EtOH): 244 nm ($\epsilon$10,240)
IR (KBr): see FIG. 3
MS (FAB): (M+H) m/z 704

Table II summarizes the $^1H$ and $^{13}C$ nuclear magnetic resonance (NMR) spectral data for A83543M (in acetone-$d_6$).

TABLE II $^1H$ and $^{13}C$ NMR data of A83543M in acetone-$d_6$

| Position | $^{13}C$ | $^1H$* |
|---|---|---|
| 1 | 172.65 | — |
| 2 | 34.53 | 3.08/2.44 |
| 3 | 48.80 | 2.94 |
| 4 | 42.36 | 3.50 |
| 5 | 129.80 | 5.87 |
| 6 | 130.34 | 5.91 |
| 7 | 42.05 | 2.14 |
| 8 | 37.21 | 1.97/1.36 |
| 9 | 77.04 | 4.34 |
| 10 | 38.30 | 2.36/1.36 |
| 11 | 47.12 | 0.94 |
| 12 | 50.44 | 2.87 |
| 13 | 148.34 | 7.05 |
| 14 | 144.93 | — |
| 15 | 203.08 | — |
| 16 | 48.36 | 3.31 |
| 17 | 81.22 | 3.55 |
| 18 | 35.15 | 1.52 |
| 19 | 22.38 | 1.78/1.17 |
| 20 | 31.09 | 1.50 |
| 21 | 76.82 | 4.66 |
| 22 | 29.11 | 1.48 |
| 23 | 9.57 | 0.80 |
| 24 | 16.44 | 1.13 |
| 1' | 96.46 | 4.84 |
| 2' | 82.50 | 3.31 |
| 3' | 72.23 | 3.72 |
| 4' | 84.61 | 2.94 |
| 5' | 68.40 | 3.48 |
| 6' | 18.34 | 1.19 |
| 2'-$OCH_3$ | 59.08 | 3.44 |
| 4'-$OCH_3$ | 60.72 | 3.50 |
| 1" | 104.15 | 4.48 |
| 2" | 31.78 | 1.88/1.42 |
| 3" | 29.11 | 2.11/1.23 |
| 4" | 61.86 | 2.02 |
| 5" | 76.55 | 3.27 |
| 6" | 19.34 | 1.22 |
| NH—$CH_3$ | 34.16 | 2.34 |

*Shifts were taken from the $^1H$ spectrum or 2D $^1H/^{13}C$ one bond correlation.

Characteristics of A83543N

Figure 5:
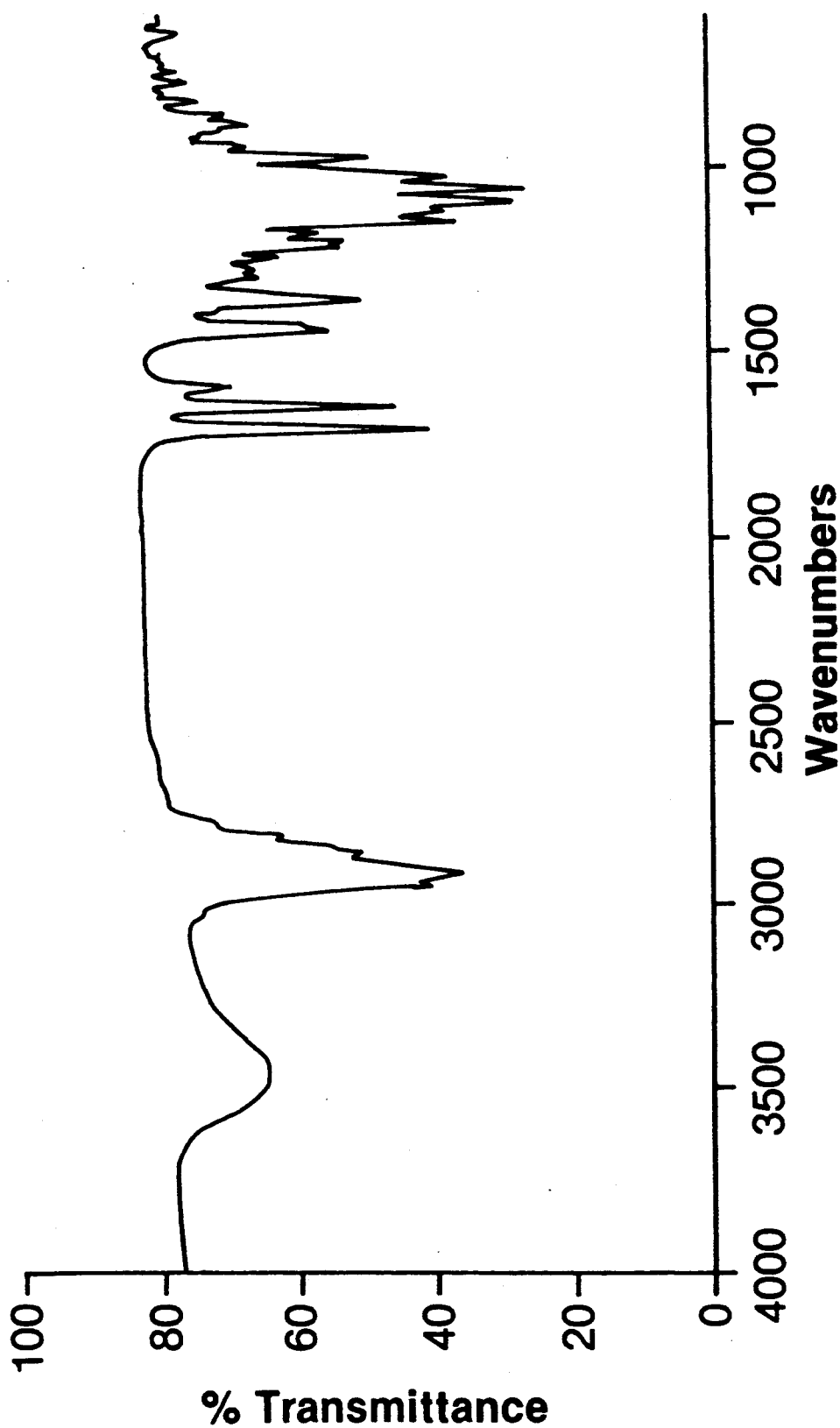
FIG. 5 shows the infrared absorption spectrum of A83543N in KBr.
Figure 6:
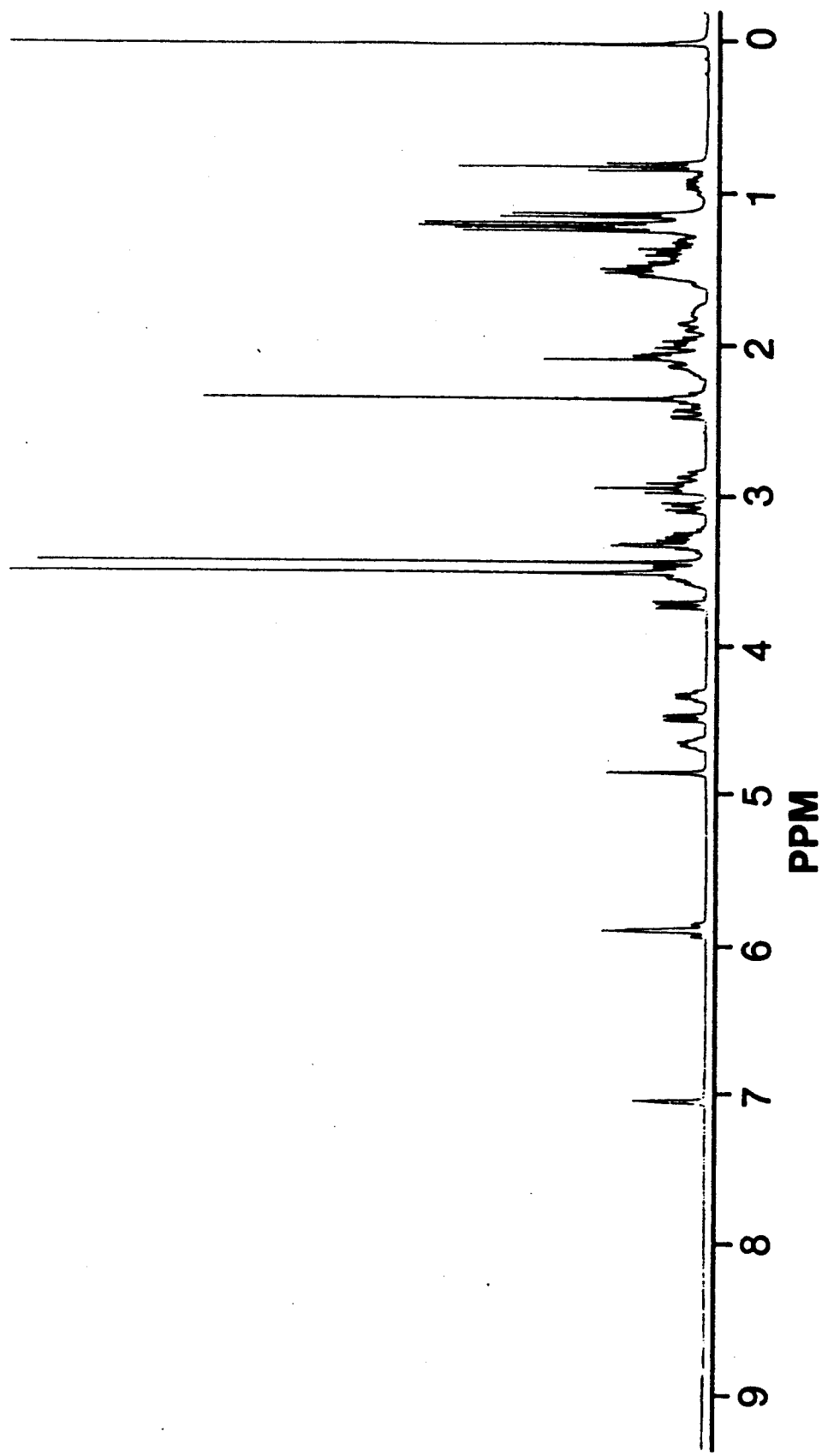
FIG. 6 shows the proton nuclear magnetic resonance spectrum (300 MHz) of A83543N in acetone d₆.

A83543N has the following characteristics:
Molecular weight: 717
Empirical formula: $C_{40}H_{63}NO_{10}$
UV (EtOH): 244 nm ($\epsilon$10,446)
IR (KBr): see FIG. 5
MS (FAB): (M+H) m/z 718

Table III summarizes the $^1H$ and $^{13}C$ nuclear magnetic resonance (NMR) spectral data for A83453N (in acetone-$d_6$).

TABLE III $^1H$ and $^{13}C$ NMR data of A83543N in acetone-$d_6$

| Position | $^{13}C$ | $^1H$* |
|---|---|---|
| 1 | 172.65 | — |
| 2 | 34.41 | 3.06/2.43 |
| 3 | 50.00 | 2.90 |
| 4 | 42.85 | 3.45 |
| 5 | 123.38 | 5.55 |
| 6 | 137.25 | — |
| 7 | 45.39 | 2.18 |
| 8 | 35.67 | 2.01/1.46 |
| 9 | 76.78 | 4.32 |
| 10 | 38.65 | 2.37/1.40 |
| 11 | 47.07 | 1.03 |
| 12 | 50.07 | 2.78 |
| 13 | 148.41 | 7.03 |
| 14 | 145.17 | — |
| 15 | 203.14 | — |
| 16 | 48.44 | 3.31 |
| 17 | 81.14 | 3.56 |
| 18 | 35.13 | 1.51 |
| 19 | 22.44 | 1.81/1.20 |

TABLE III-continued $^1$H and $^{13}$C NMR data of A83543N in acetone-$d_6$

| Position | $^{13}$C | $^1$H* |
|---|---|---|
| 20 | 31.05 | 1.51 |
| 21 | 76.78 | 4.65 |
| 22 | 29.11 | 1.48 |
| 23 | 9.56 | 0.81 |
| 24 | 16.41 | 1.12 |
| 6-CH$_3$ | 20.82 | 1.73 |
| 1' | 96.51 | 4.86 |
| 2' | 82.51 | 3.32 |
| 3' | 72.24 | 3.73 |
| 4' | 84.62 | 2.95 |
| 5' | 68.41 | 3.50 |
| 6' | 18.34 | 1.18 |
| 2'-OCH$_3$ | 59.09 | 3.43 |
| 4'-OCH$_3$ | 60.71 | 3.51 |
| 1" | 104.13 | 4.48 |
| 2" | 31.78 | 1.87/1.40 |
| 3" | 29.11 | 2.11/1.23 |
| 4" | 61.88 | 2.00 |
| 5" | 76.58 | 3.26 |
| 6" | 19.33 | 1.22 |
| NH—CH$_3$ | 34.18 | 2.34 |

*Shifts were taken from the $^1$H spectrum or 2D $^1$H/$^{13}$C one bond correlation.

The amino sugar can be selectively removed from A83543L to give the pseudoaglycone A83543PsaL1. This compound is a further aspect of the present invention and is shown in the following formula:

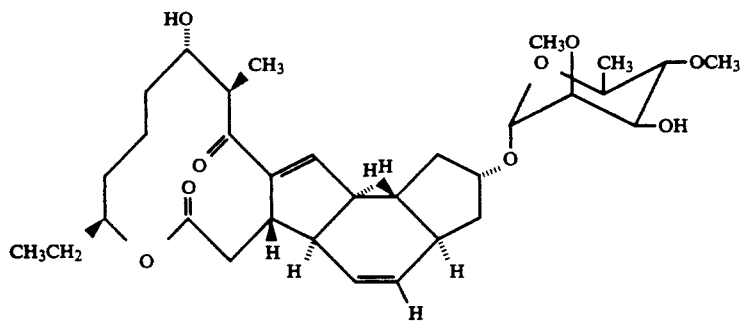

A83543PsaL1 is useful as a starting material for the preparation of known A83543 compounds that are useful as insecticides. More specifically, A83543PsaL1 may be bioconverted to A83543L and A83543N by culturing any of the known A83543-producing strains in the presence of A83543PsaL1.

For purposes of further discussion, it will be useful to divide the formula 1 compounds into two sub groups, 1A and 1B. The formula 1A compounds are A83543L, A83543M, A83543N, Compound 4, and Compound 5. The formula 1B compound is A83543PsaL1.

The formula 1A compounds can react to form various salts, which are also a part of this invention. These salts are useful, for example, in separating and purifying the formula 1A compounds. In addition, some of the salt forms may have increased water solubility. These salts are prepared using standard procedures for salt preparation. For example, A83543L can be neutralized with an appropriate acid to form an acid addition salt.

The acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic, and like acids.

A83543J-Producing Strains

The term "A83543J producing strain" means a strain of *Saccharopolyspora spinosa* derived directly or indirectly from culture A83543.1 that is capable of producing recoverable amounts of A83543J. Preferred A83543J-producing strains are NRRL 18719, NRRL 18720, and strains derived from these two strains.

For convenience in the discussions which follow, the A83543 producing strains have been given the following designations: A83543.1 and A83543.4. Also, the new A83543J-producing strains have been given the designation A83543.6 and A83543.7. Cultures A83543.1, A83543.4, A83543.6, and A83543.7 have been deposited and made a part of the stock culture collection of the Midwest Area Regional Research Center, Agricultural Research Service, United States Department of Agriculture, from which they are available to the public under the following accession numbers:

| NRRL No. | Strain No. |
|---|---|
| 18395 | A83543.1 |
| 18538 | A83543.4 |
| 18719 | A83543.6 |
| 18720 | A83543.7 |

Culture A83543.1 was obtained by chemical mutation of culture A83543, which was isolated from a soil sample collected in the Virgin Islands. Mertz and Yao, "*Saccharopolyspora spinosa* sp. nov. Isolated from Soil Collected in a Sugar Mill Rum Still," *Int'l J. of Systematic Bacteriology*, 40, 34 (1990). Cultures A83543.4 and A83543.6 are derived from culture A83543.1. Culture A83543.7 was derived from A83543.4 by chemically induced mutagensis with N methyl-N'-nitro N-nitrosoguanidine. The following data show that these isolates are all strains of *Saccharopolyspora spinosa* and have very few cultural, morphological, or biochemical differences. Except for differences in the production of the A83543 components, these isolates appear the same as the parent culture.

Cultural Characteristics

Cultures A83543.1, A83543.4, A83543.6, and A83543.7 were grown on twelve agar plating media and compared for growth, reverse color, aerial hyphae production, spore mass color, and soluble pigment production. No significant differences were observed on any of the media used. The cultures grew well on both complex and defined media. Aerial hyphae were produced on most of the media used. The aerial spore mass color was predominantly white, and the reverse side was yellow to yellow-brown. No distinctive pigmentation was present; however, a soluble brown pigment was released into some media. These cultural characteristics are the same as presented in the original taxonomic description of A83543.1. See Mertz and Yao, *Int'l J. of Systematic Bacteriology*, 40, 34 (1990).

Morphological Characteristics

No significant differences were observed between any of the strains compared. Well-formed aerial hyphae, which were segmented into long chains of spores arranged as hooks and open loops, were present on most of the media. Spirals were also observed, but they were short and incomplete. The general morphology was rectus flexibilis. Aerial hyphae of each of the strains had a distinctive bead-like appearance, with many empty spaces in the spore chain. This feature demonstrated that a spore sheath encased the spore chain, which is a distinctive feature of the genus Saccharopolyspora.

Physiological Characteristics

Fatty acid analysis from each of the strains were compared. Cells were grown for 96 hours at 28° C. in trypticase soy broth (Difco Laboratories, Detroit, Mich.). Fatty acid methyl esters were analyzed by gas-liquid chromatography with a model 5898A computer-controlled gas-liquid chromatogrphy system (Hewlett-Packard Co., Palo Alto, Calif.). See Miller and Berger, "Bacterial Identification by Gas Chromatography of Whole Cell Fatty Acids," Hewlett-Packard Application Note 228-41. These results are presented in Table V.

TABLE V

| Fatty Acid | Percentage Fatty Acid Composition of A83543 Strains | | | |
|---|---|---|---|---|
| | A83543.1 | A83543.4 | A83543.6 | A83543.7 |
| 15:0 ISO | 15.95 | 22.47 | 16.49 | 17.00 |
| 16:0 ISO | 28.71 | 22.00 | 25.76 | 27.39 |
| 16:1 Cis 9 | — | 1.35 | — | — |
| 15:0 ISO 2OH | 2.67 | 2.02 | 3.87 | 3.95 |
| 16:0 | 1.20 | 0.69 | 0.63 | 0.60 |
| 17:1 ISO F[1] | 5.52 | 8.62 | 7.54 | 5.51 |
| 17:0 Iso | 13.55 | 20.67 | 16.40 | 13.89 |
| 17:0 Anteiso | 8.39 | 3.94 | 4.69 | 5.18 |
| 17:1 B | 4.14 | 3.97 | 4.65 | 6.68 |
| 17:1 C | 2.52 | 2.88 | 4.90 | 5.53 |
| 17:0 | 4.26 | 1.49 | 3.13 | 3.84 |
| 16:1 2OH | 1.87 | 1.52 | 1.93 | 0.92 |
| 18:1 Iso F | 6.55 | 4.16 | 5.82 | 6.00 |
| 18:1 Cis 9 | 0.34 | 1.03 | 0.64 | 0.63 |

[1]F, B, and C indicate double bond positions or configurations that are unknown.

Figure 7:
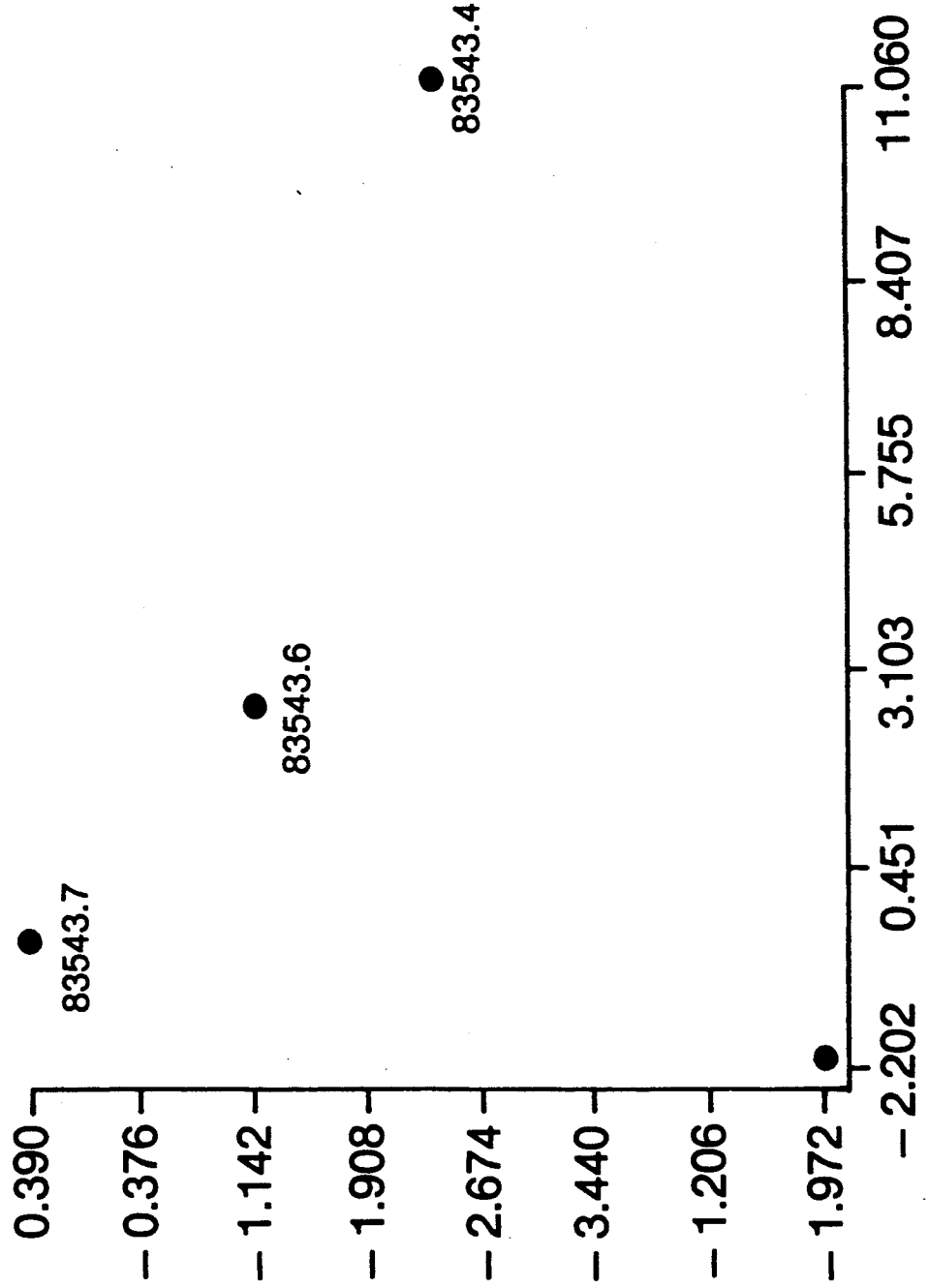
FIG. 7 shows the principle component plot of fatty acid analyses for strains A83543.1, A83543.4, A83543.6 and A83543.7.

Principal component analysis is a branch of multivariate statistics that deals with internal relationships of a set of variables. In this analysis, the greatest amount of variance within the original data or test results is expressed as principal components. Alderson, "The Application and Relevance of Nonheirarchic Methods in Bacterial Taxonomy," in *Computer Assisted Bacterial Systematics* 227 (1985). A plot showing scatter or variability can be constructed. Relationships can be evaluated by examining the variance, and a microbial population characterized. A two dimensional principal component plot from the fatty acid analyses of strains A83543.1, A83543.4, A83543.6 and A83543.7 is shown in FIG. 7. The values refer to the degrees of separation between the strains involved. The differences between the strains are not taxonomically significant.

As is the case with other organisms, the characteristics of the A83543-producing and A83543J-producing strains are subject to variation. Thus, mutants of these strains may be obtained by physical and chemical methods known in the art. For example, other strains may be obtained by treatment with chemicals such as N methyl N'-nitro-N-nitrosoguanidine. Natural and induced mutants of the *Saccharopolyspora spinosa* strains NRRL 18719 and NRRL 18720, which retain the characteristic of producing recoverable amounts of a formula 2 compound, are applicable in the present invention.

Preparation of New Compounds by Fermentation

One aspect of the present invention is the production of a compound of formula 2 by culturing an A83543J-producing strain of *Saccharopolyspora spinosa* in a suitable culture medium. Suitable strains are NRRL 18719, NRRL 18720, and any other A83543J-producing mutant of culture A83543.1. An "A83543J-producing mutant of culture A83543.1" is any strain derived directly or indirectly from A83543.1 that is capable of producing recoverable amounts of A83543J. After production, the formula 2 compounds may be separated from the culture medium using various isolation and purification procedures as described hereinafter.

For economy in production, optimal yield, and ease of product isolation, certain culture media are preferred. For example, preferred carbon sources in large scale fermentation are glucose and methyl oleate, although ribose, xylose, fructose, galactose, mannose, mannitol, maltose, soluble starch, potato dextrin, oils such as soybean oil and the like can also be used. Preferred nitrogen sources are cottonseed flour, peptonized milk and corn steep liquor, although fish meal, digested soybean meal, yeast extract, enzyme-hydrolyzed casein, beef extract, and the like can also be used. Among the nutrient inorganic salts which can be incorporated in the culture media are the customary soluble salts capable of yielding zinc, sodium, magnesium, calcium, ammonium, chloride, carbonate, sulfate, nitrate and like ions. Essential trace elements necessary for the growth and development of the organism should also be included in the culture medium. Such trace elements commonly occur as impurities in other substituents of the medium in amounts sufficient to meet the growth requirements of the organism.

Usually, if foaming is a problem, small amounts (i.e., 0.2 ml/L) of an antifoam agent such as polypropylene glycol may be added to large scale fermentation media. In the case of the A83543-producing cultures, however, conventional defoamers inhibit A83543 production. Foaming can be controlled by including soybean oil or PLURONIC L-101 (BASF, Parsippany, NJ) in the medium (1-3%). Additional oil may be added if foaming develops.

For production of substantial quantities of a formula compound, submerged aerobic fermentation in stirred bioreactors is preferred; however, small quantities of a formula 2 compound may be obtained by shake flask culture. Because of the time lag in production commonly associated with inoculation of large bioreactors with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger bioreactor. The vegetative inoculum medium can be the same as that used for larger fermentations, but other media are also suitable.

The formula 2 compounds are produced by the A83543J-producing strains when grown at temperatures between about 24° and about 33° C. Optimum temperatures for production appear to be about 28°-30° C.

As is customary in submerged aerobic culture processes, sterile air is blown into the vessel from the bottom while the medium is stirred with conventional turbine impellors. In general, the aeration rate and agitation rate should be sufficient to maintain the level of dissolved oxygen at or above 60% of air saturation, preferably above 65%, with an internal vessel pressure of about 0.34 atmospheres.

Production of the formula 2 compounds can be followed during the fermentation by testing extracts of the broth. A preferred method for following the production is analysis of the broth extracts by high performance liquid chromatography (HPLC). A suitable system for analysis is described in Example 1.

Following the production in shake flasks or in stirred reactors, the formula 2 compounds can be recovered from the fermentation medium by methods described herein. The compounds produced during fermentation of the A83543J-producing strain occur in both the mycelia and the broth. The formula 2 compounds are lipophilic; when a substantial amount of oil is used in the fermentation, whole broth extraction is more efficient. If only small amounts of oil are used, the major amounts of the formula 2 compounds are present in the mycelia. In that case, more efficient recovery of the formula 2 compounds is accomplished by initially filtering the medium to separate the broth from the mycelial mass (the biomass).

The formula 2 compounds can be recovered from the biomass by a variety of techniques. A suitable technique involves washing the separated biomass with water to remove remaining broth, mixing the biomass with a polar solvent in which the formula 2 compounds are soluble, e.g. methanol or acetone, separating and concentrating the solvent, extracting the concentrate with a non-polar solvent, such as heptane, and/or adsorbing it onto a reverse-phase silica gel adsorbent, such as reverse phase $C_8$ or $C_{18}$ resin, or a high porous polymer such as HP-20 or HP 20SS (Mitsubishi Chemical Industries Co., Ltd., Japan). The active material is eluted from the adsorbent with a suitable solvent such as, for example, acetonitrile:methanol mixtures, optionally containing small amounts of THF.

A preferred technique for isolating the formula 2 compounds from the biomass involves adding an equal volume of acetone to the whole broth, filtering the mixture in a ceramic filter to remove the biomass, and extracting the filtrate with ethyl acetate. The ethyl acetate extract is concentrated in vacuo to remove the acetone, and the aqueous layer is separated from the organic layer. The ethyl acetate solution is further concentrated in vacuo, and the concentrate is extracted with dilute aqueous acid (pH 3). The formula 2 compounds may be further purified by chromatography as described herein.

A more preferred technique for isolating the formula 2 compounds from the biomass involves adding an equal volume of acetone to the whole broth, filtering the mixture in a ceramic filter to remove the biomass, and adjusting the pH of the filtrate to about pH 7 to pH 10. This solution is applied to a column of HP-20SS (Mitsubishi Chemical Industries Co., Ltd., Japan) and the column is washed with a mixture of methanol, acetonitrile, and water (1:1:2). The formula 2 compounds are eluted with a 95:5 mixture of methanol/acetonitrile (1:1) containing 0.1% ammonium acetate (pH 8.1). The fractions containing the formula 2 compounds are combined, concentrated, and optionally lyophilized.

The formula 2 compounds are further purified by silica gel chromatography. The methanol concentrates containing the formula 2 compounds from the HP-20SS column described above may be diluted with acetonitrile to precipitate impurities. These impurities are removed by filtration and the filtrate is concentrated to a residue. The residue is dissolved in methylene chloride and chromatographed on a silica gel column (Silica Gel 62, 60–200 mesh, EM Science, Gibbstown, NJ), eluting with a mixture of acetonitrile and methanol (9:1). The fractions containing the formula 2 compounds are concentrated to dryness. The formula 2 compounds may be further purified using reverse-phase HPLC as described in Example 4.

Alternatively, the culture solids, including medium constitutents and mycelium, can be used without extraction or separation, but preferably after removal of water, as a source of the formula 2 compounds. For example, after production of the formula 2 compounds, the whole fermentation broth can be dried by lyophilization, by drum-drying, or by azeotropic distillation and drying. The dried broth can then be used directly, for example, by mixing it directly into feed premix or into formulations for sprays and powders.

Chemical Demethylation

Alternatively, A83543M and A83543N may be prepared by reacting A83543J and A83543L, respectively, with iodine and sodium acetate. The reaction is carried out in a polar organic solvent, such as methanol, or a mixture of a polar organic solvent and water, such as aqueous methanol. The reaction is preferably carried out at a temperature from about 30° C. to about 70° C. for about 2 to about 6 hours. A83543M and A83543N may be further demethylated to Compounds 4 and 5, respectively, by treatment with iodine and sodium methoxide in methanol.

Preparation of Pseudoaglycone

A83543L is used to prepare A83543PsaL1 by the reaction of A83543L with acid. Suitable acids include hydrochloric and sulfuric, the preferred acid for the transformation is sulfuric. The reaction is preferably carried out in a polar organic solvent, a mixture of a polar organic solvent and water, or water. Suitable organic solvents include methanol, THF, acetonitrile and dioxane. The preferred solvents for the transformation are a mixture of methanol and water or water. The reaction may be carried out at a temperature from about 25° C. to about 95° C., preferably at 80° C.

Insecticidal Activity

The formula 1A compounds are useful for the control of insects. Therefore, a further aspect of the present invention is directed to methods for inhibiting an insect which comprises applying to the locus of the insect an insect-inhibiting amount of a formula 1A compound.

The "locus" of the insect refers to the environment in which the insect lives or where its eggs are present, including the air surrounding it, the food it eats, or objects which it contacts. For example, plant-ingesting insects can be controlled by applying the active compound to plant parts which the insects eat or inhabit, particularly the foliage.

The term "inhibiting an insect" refers to a decrease in the number of living insects or to a decrease in the number of viable insect eggs. The extent of reduction accomplished by a compound depends, of course, upon the application rate of the compound, the particular compound used, and the target insect species. At least an insect-inactivating amount should be used.

The term "insect-inactivating amount" is used to describe the amount which is sufficient to cause a measurable reduction in the treated insect population. Generally, an amount in the range from about 1 to about 1,000 ppm (or 0.01 to 1 kg/ha) of active compound is used.

The formula 1A compounds show activity against a number of insects. More specifically, the compounds show activity against tobacco budworm, which is a member of the insect order Lepidoptera. Other typical members of this order are southern armyworm, beet armyworm, codling moth, cutworms, clothes moths, Indian meal moth, leaf rollers, corn ear worm, cotton bollworm, European corn borer, imported cabbage worm, cabbage looper, pink bollworm, bagworms, eastern tent caterpillar, sod webworm, and fall armyworm.

The formula 1A compounds also show activity against leaf hoppers, which is a member of the insect order Homoptera. Other members of this order include cotton aphid, plant hoppers, pear psylla, apple sucker, scale insects, whiteflies, and spittle bugs, as well as a number of other host-specific aphid species.

In addition, the formula 1A compounds show activity against stable flies, blowflies, and mosquitoes, which are members of the insect order Diptera. Another typical member of this order is the common house fly.

The formula 1A compounds are useful for reducing populations of insects and are used in a method of inhibiting an insect population which comprises applying to a locus of the insect an effective insect-inactivating amount of a formula 1A compound. In one preferred embodiment, the present invention is directed to a method for inhibiting a susceptible insect of the order Lepidoptera which comprises applying to a plant an effective insect inactivating amount of a formula 1A compound in accordance with the present invention. Another preferred embodiment of the invention is directed to a method of inhibiting biting flies of the order Diptera in animals which comprises administering an effective pest-inhibiting amount of a formula 1A compound orally, parenterally, or topically to the animal. In another preferred embodiment, the present invention is directed to a method for inhibiting a susceptible insect of the order Homoptera which comprises applying to a plant an effective insect-inactiviating amount of a formula 1A compound.

Mite/Insect Screen

The formula 1A compounds were tested for miticidal and insecticidal activity in the following mite/insect screen. Each test compound was formulated by dissolving the compound in an acetone-alcohol (1:1) mixture containing 23 g of TOXIMUL R (sulfonate/nonionic emulsifier blend) and 13 g of TOXIMUL S (sulfonate/nonionic emulsifier blend) per liter. These mixtures were then diluted with water to give the indicated concentrations.

Two-spotted spider mites and cotton aphids were introduced on squash cotyledons and allowed to establish on both leaf surfaces. The leaves were then sprayed with 5 ml of test solutions using a DeVilbiss atomizing sprayer at 10 psi. Both surfaces of the leaves were covered until run off and then allowed to dry for one hour. After standard exposure periods percent mortality was evaluated. Additional insects were evaluated using similar formulations and evaluation procedures. The results are reported in Table VI. The following abbreviations are used:

TABLE VI

| Abbreviation | Pest | Scientific Name |
| --- | --- | --- |
| ALH | Aster Leafhopper | Macrosteles fascifrons |
| BAW | Beet Armyworm | Spodoptera exiqua |
| CA | Cotton Aphid | Aphis gossypii Glover |
| GECR | German Cockroach | Blattella germanica |
| NEM | Rootknot Nematode | Meliiodyne spp. |
| SCRW | Southern Corn Rootworm | Diabrotica undecimpunctata howardi |
| TBW | Tobacco Budworm | Heliothis virescens |
| TSSM | Two-spotted Spider Mite | Tetranychus urticae |

| Activity of Formula 1A Compounds in Insect/Mite Screen | | | | | |
| --- | --- | --- | --- | --- | --- |
| | Exposure | | % Inhibition[b] | | |
| Pest | Rate[a] | Exposure period | A83543L | A83543M | A83543N |
| ALH | 200 | 24 hr | 100 | 60 | 100 |
| | 400 | 24 hr | 100 | 100 | 100 |
| BAW | 200 | 6 day | 100 | 0 | 90 |
| | 400 | 6 day | 100 | 0 | 100 |
| CA | 200 | 4–5 day | 0 | 0 | 0 |
| | 400 | 4–5 day | 0 | 0 | 0 |
| GECR | 200 | 7 day | 40 | 0 | 0 |
| | 400 | 7 day | 0 | 0 | 0 |
| | 200 | 21 day | 100 | 20 | 0 |
| | 400 | 21 day | 100 | 40 | 0 |
| NEM | 200 | 11 day | 0 | 0 | 0 |
| | 400 | 11 day | 0 | 0 | 0 |
| SCRW | 200 | 11 day | 0 | 0 | 0 |
| | 400 | 11 day | 0 | 0 | 0 |
| TBW | 200 | 6 day | 100 | 70 | 100 |
| | 400 | 6 day | 100 | 100 | 100 |
| TSSM | 200 | 4–5 day | 0 | 0 | 0 |
| | 400 | 4–5 day | 0 | 0 | 0 |

[a] rate in ppm
[b] % inhibition as a mean of single replicates tests

The formula 1A compounds were evaluated in the following assay to determine the $LD_{50}$ against neonate tobacco budworm (Heliothis virescens). A petri dish (100 mm × 20 mm) is inverted and the lid lined with a #1 qualitative filter paper. Ten neonate larvae are placed in each dish and a 1 ml test solution is pipetted onto the insects. The petri dish bottom is then placed on the lid to contain the larvae. At 1 hr. after treatment, a small piece of Heliothis diet (modified shurry, Southland Products, Lake Village, AR) is added to each dish. The mortality is evaluated at 24 and 48 hours. Each test is run in triplicate. The results are shown in Table VII.

TABLE VII

| Activity of Formula 1A Compounds Against Neonate Tobacco Budworm | |
| --- | --- |
| Compound | $LD_{50}$ (ppm)[a] |
| A83543L | 26.0 |
| A83543M | 22.6 |
| A83543N | 40.0 |

[a] mean of two tests

Insecticidal Compositions

The formula 1A compounds of this invention are applied in the form of compositions, which are also a part of this invention. These compositions comprise an insect-inactivating amount of a formula 1A compound in a phytologically acceptable inert carrier. The active component, the formula 1A compound, may be present as a single formula 1A compound, a mixture of two or more formula 1A compounds; a mixture of a formula 1A compound with one or more of the A83543 components; or a mixture of the formula 1A compounds together with the dried portion of the fermentation medium in which it is produced.

Compositions are prepared according to procedures and formulas which are conventional in the agricultural chemical art, but which are novel and important because of the presence of one or more of the compounds of this invention. The compositions are either concentrated formulations which are dispersed in water for application or dust or granular formulations which are applied without further treatment.

The dispersions in which the compound or crude dried material are applied are most often aqueous suspensions or emulsions prepared from concentrated formulations of the compounds or crude material. Such water-soluble, water-suspendible, or emulsifiable formulations are either solids (usually known as wetable powders) or liquids (usually known as emulsifiable concentrates or aqueous suspensions).

Wetable powders, which may be compacted to form water disperable granules, comprise an intimate mixture of the active compound, an inert carrier, and surfactants. The concentration of the active compound is usually from about 1% to about 90% by weight. The inert carrier is usually chosen from among attapulgite clays, the montmorillonite clays, the diatomaceous earths or the purified silicates.

Effective surfactants, comprising from about 0.5% to about 10% of the wetable powder are found among the sulfonated lignins, the condensed naphthalenesulfonates, the alkylbenzenesulfonates, the alkylsulfates, and non-ionic surfactants such as ethylene oxide adducts of alkylphenols.

Emulsifiable concentrates of the compounds comprise a convenient concentration of a compound, such as from about 50 to about 500 grams per liter of liquid, equivalent to about 10% to about 50%, dissolved in an inert carrier which is either a water-miscible solvent or mixture of a water-immiscible organic solvent and emulsifiers. Useful organic solvents include aromatics, especially the xylenes, and petroleum fractions, especially high-boiling naphthlenic and olefinic portions of petroleum such as heavy or aromatic naptha. Other organic solvents may also be used, such as the terpenic solvents, including rosin derivatives, aliphatic ketones such as cyclohexanone, and complex alcohols such as 2-ethoxyethanol. Suitable emulsifiers for emulsifiable concentrates are chosen from conventional nonionic surfactants, such as those mentioned above.

Aqueous suspensions comprise suspensions of water-insoluble compounds of this invention dispersed in an aqueous vehicle at a concentration in the range from about 5% to about 50% by weight. The suspensions are prepared by finely grinding the compound, and vigorously mixing it into a vehicle comprised of water and surfactants chosen from the same types discussed above. Inert ingredients, such as inorganic salts and synthetic or natural gums may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The formula 1A compounds may also be applied as granular compositions, which are particularly useful for applications to the soil. Granular compositions usually contain from about 0.5% to about 10% by weight of the formula 1A compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size in the range of from about 0.5 to 3 mm. Such compositions may also be formulated by making a dough or paste of the carrier, drying the combined mixture of the active ingredient in the dough or paste, and crushing the dried composition to obtain the desired granular particle size.

Dusts containing the compound are prepared by intimately mixing the compound in powdered form with a suitable dust agricultural carrier, such as kaolin clay, ground volanic rock, and the like. Dusts can suitably contain from about 1% to about 10% of the formula 1A compound.

It is equally practical, when desirable for any reason, to apply the compound in the form of a solution in an appropriate organic solvent, usually a bland petroleum oil, such as the spray oils, which are widely used in agricultural chemistry.

Insecticides are usually applied in the form of a dispersion of the active ingredient in a liquid carrier. It is conventional to refer to application rates in terms of the concentration of active ingredient in the carrier. The most widely used carrier is water.

The formula 1A compounds can also be applied in the form of an aerosol composition. In such compositions the active compound is dissolved in an inert carrier, which is a pressure-generating propellent mixture. The aerosol composition is packaged in a container from which the mixture is dispersed through an atomizing valve. Propellent mixtures comprise either low-boiling halocarbons, which may be mixed with organic solvents, or aqueous suspensions pressurized with inert gases or gaseous hydrocarbons.

The amount of compound to be applied to the loci of insects is not critical and can readily be determined by those skilled in the art in view of the examples provided. In general, concentrations of from about 10 ppm to about 5,000 ppm of the formula 1A compound are expected to provide good control. With many of the compounds, concentrations of from about 100 to about 1,000 ppm will suffice. For field crops, such as soybeans and cotton, a suitable application rate for the compounds is about 0.01 to about 1 kg/ha, typically applied in 5 to 50 gal/A of spray formulation. The locus to which a formula 1A compound is applied can be any locus inhabited by an insect, for example vegetable crops, fruit and nut trees, grape vines and ornamental plants.

Ectoparasiticide Activity

The formula 1A compounds are also active against members of the insect order Diptera. Tables VIII and IX summarize the in vitro studies of the formula 1A compounds against blowfly larvae and adult stable fly.

TABLE VIII

Activity of Formula 1A Compounds Against Blowfly Larvae

| Compound | Activity rate (ppm) | % mortality |
|---|---|---|
| A83543L | 5 | 90 |

TABLE IX

Activity of Formula 1A Compounds Against Adult Stablefly

| | | Activity % mortality | |
|---|---|---|---|
| Compound | rate (ppm) | 24 hr | 48 hr |
| A83543L | 5 | 70 | 100 |
| A83543M | 5 | 60 | 100 |
| A83543N | 5 | 20 | 90 |

Ectoparasiticidal Methods

The ectoparasiticidal method of this invention is carried out by administering a formula 1A compound to host animals to control insect parasites. Administration to the animal may be by the dermal, oral, or parenteral routes.

Parasitic insects include species that are bloodsucking as well as flesh eating and are parasitic during all of their life cycle or only part of their life cycle, such as only the larval or only the adult stage. Representative species include the following:

| | |
|---|---|
| horse fly | *Tabanus spp.* |
| stable fly | *Stomoxys calcitrans* |
| black fly | *Simulium spp.* |
| horse sucking louse | *Haematopinus asini* |
| horn fly | *Haematobia irritans* |
| cattle biting louse | *Bovicola bovis* |
| shortnosed cattle louse | *Haematopinus eurysternus* |
| longnosed cattle louse | *Linognathus vituli* |
| tsetse fly | *Glossina spp.* |
| cattle tick | *Boophilus microplus* and *B. decoloratus* |
| Gulf Coast tick | *Amblyomma maculatum* |
| Lone Star tick | *Amblyomma americanum* |
| ear tick | *Otobius meqnini* |
| Rocky Mountain wood tick | *Dermacentor andersoni* |
| screwworm fly | *Cochliomyia hominivorax* |
| assassin bug | *Reduvius spp.* |
| mosquito | *Culiseta inornata* |
| brown ear tick | *Rhipicephalus appendiculatus* |
| African red tick | *Rhipicephalus evertsi* |
| bont tick | *Amblyomma sp.* |
| bont legged tick | *Hyalomma sp.* |
| hog louse | *Haematopinus suis* |
| chigoe | *Tunga penetrans* |
| body louse | *Haematopinus ovillus* |
| foot louse | *Linognathus pedalis* |
| sheep ked | *Melophagus ovinus* |
| greenbottle fly | *Phaenicia sericata* |
| black blow fly | *Phormia regina* |
| secondary screw-worm | *Cochliomyia macellaria* |
| sheep blow fly | *Phaenicia cuprina* |
| bed bug | *Cimex lectularius* |
| Southern chicken flea | *Echidnophaga gallinacea* |
| fowl tick | *Argas persicus* |
| dog flea | *Ctenocephalis canis* |
| American dog tick | *Dermacentor variabilis* |
| brown dog tick | *Rhipicephalus sanguineus* |

The method of the invention may be used to protect economic and companion animals from ectoparasites. For example, the compound may beneficially be administered to horses, cattle, sheep, pigs, goats, dogs, cats and the like, as well as to exotic animals such as camels, llamas, deer and other species which are commonly referred to as wild animals. The compound may also beneficially be administered to poultry and other birds, such as turkeys, chickens, ducks and the like. Preferably, the method is applied to economic animals, and most preferably to cattle and sheep.

Ectoparasiticidal Compositions

This invention also relates to compositions for controlling a population of insect ectoparasites which consume blood of a host animal. These compositions may be used to protect economic, companion, and wild animals from ectoparasites. The compositions may also beneficially be administered to poultry and other birds. Preferably, the method is applied or the compositions are used to protect economic animals, and most preferably to cattle and sheep. The rate, timing and manner of effective application will vary widely with the identity of the parasite, the degree of parasital attack and other factors. Applications can be made periodically over the entire life span of the host, or for only peak season of parasitic attack. In general ectoparasite control is obtained with topical application of liquid formulations containing from about 0.0005 to about 95% of the formula 1A compound, preferably up to 5%, and most preferably up to 1% of a formula 1A compound. Effective parasite control is achieved at an administration rate from about 5 to about 100 mg/kg.

The formula 1A compounds are applied to host animals by conventional veterinary practices. Usually the compounds are formulated into ectoparasiticidal compositions which comprise a formula 1A compound and a physiologically-acceptable carrier. For example, liquid compositions may be simply sprayed on the animals for which ectoparasiticidal control is desired. The animals may also treat themselves by such devices as back rubbers which may contain the formula 1A compound and a cloth, for example, which the animal may walk against and contact. Dip tanks are also employed to administer the active agent to the host animal.

Oral administration may be performed by mixing the compound in the animal's feed or drinking water, or by administering dosage forms such as tablets, capsules, boluses or implants. Percutaneous administration is conveniently accomplished by subcutaneous, intraperitoneal, and intravenous injection of an injectable formulation.

The formula 1A compounds can be formulated for oral administration in the usual forms, such as drenches, tablets or capsules. Such compositions, of course, require orally-acceptable inert carriers. The compounds can also be formulated as an injectable solution or suspension, for subcutaneous, dermal, intraruminal, intraperitoneal, intramuscular, or intravenous injection. In some applications the compounds are conveniently formulated as one component of a standard animal feed. In this embodiment it is usual to formulate the present compound first as a premix in which the compound is disbursed in a liquid or particulate solid carrier. The premix can contain from about 2 to about 250 g of formula 1A compound per pound of mix. The premix is in turn formulated into the ultimate feed by conventional mixing.

Because ectoparasitic attack generally takes place during a substantial portion of the host animal's life span, it is preferred to administer the compounds of the present invention in a form to provide sustained release over a period of time. Conventional procedures include the use of a matrix which physically inhibits dissolution, where the matrix is a waxy semi-solid, such as the vegetable waxes, or a high molecular weight polyethylene glycol. A good way to administer the compounds is by means of a sustained action bolus, such as those of Laby, U.S. Pat. No. 4,251,506 and Simpson, British Patent No. 2,059,767. For such a bolus the compound would be encapsulated in a polymeric matrix such as that of Nevin, U.S. Pat. No. 4,273,920. Sustained release of the compounds of the present invention can also be achieved by the use of an implant such as from a silicone-containing rubber.

In order to illustrate more fully the operation of this invention, the following examples are provided:

EXAMPLE 1

A83543 Assay Method

The following analytical high performance liquid chromatography (HPLC) method is useful for monitoring a fermentation for the production of A83543L, A83543M, A83543N, and other A83543 components:

A sample of the whole broth is diluted with three volumes of acetonitrile to extract the factors from the mycelia. The resulting solution is then filtered through a 0.45 micron PTFE filter to remove particulate matter prior to injection into the HPLC assay system. A solution of purified A83543A at a concentration of 100 $\mu$g/ml in methanol is used as an external standard for the assay and peak areas of all A83543 components are related back to this calibration standard to determine concentrations of individual factors.

HPLC System:
- Column Support: 4.6×100 mm column, ODS AQ, 5$\mu$ spherical particles, 120Å pore (YMC, Inc., Morris Plains, N.J.)
- Mobile Phase: $CH_3CN/MeOH/H_2O$ (40/40/20) containing 0.05% ammonium acetate
- Flow Rate: 3 mL/min
- Detection: UV at 250 nm
- Retention Times:
    - A83543A 9.1 min
    - A83543J 5.7 min
    - A83543L 7.3 min
    - A83543M 2.6 min
    - A83543N 3.3 min

EXAMPLE 2

Preparation of A83543J, A83543L, A83543M, and A83543N with Culture A83543.6

A. Shake-flask Fermentation

The culture *Saccharopolyspora spinosa* NRRL 18719, either as a lyophilized pellet or as a suspension maintained in liquid nitrogen, was used to inoculate a vegetative medium having the following composition:

| Vegetative Medium | |
|---|---|
| Ingredient | Amount (g) |
| Trypticase broth* | 30 |
| Yeast extract | 3 |
| MgSO$_4$.7H$_2$O | 2 |
| Glucose | 5 |
| Maltose | 4 |
| Deionized water | q.s. 1 L |

Autoclave 30 min at 120° C.
*Baltimore Biological Laboratories, Cockeysville, MD Slants or plates can be prepared by adding 2.5% agar to the vegetative medium. The inoculated slant is incubated at 30° C. for about 10 to about 14 days. The mature slant culture is scraped with a sterile tool to loosen the spores and to remove and macerate the mycelial mat. About one-fourth of the loosened spores and culture growth thus obtained is used to inoculate 50 ml of a first stage vegetative medium. Alternatively, the first-stage medium may be inoculated from a liquid nitrogen ampoule.

When the culture is maintained in liquid nitrogen, ampoules are prepared by homogenizing a vegetative culture (48-72 hours incubation, 30° C.), diluting 1:1 (volume:volume) with a sterile suspending agent, and dispensing into sterile tubes (1.5 ml/tube). The suspending agent contains lactose (100 g), glycerol (200 ml), and deionized water (q.s. to 1 L).

A liquid nitrogen ampoule is used to inoculate 100 ml of vegetative medium in 500-ml Erlenmeyer flasks (or 50 ml of medium in 250-ml flasks). The cultures are incubated at 30° C. for 48 hours on a shaker orbiting in a two-inch (5.08 cm) circle at 260 rpm.

The incubated culture (10% v/v inoculum) is used to inoculate 50 ml or 100 ml, dependent on the size of the Erlenmeyer flask, of a production medium having the following composition:

| Production Medium | |
|---|---|
| Ingredient | Amount (g) |
| Glucose | 80 |
| Peptonized milk* | 20 |
| Cottonseed flour** | 30 |
| Corn steep liquor | 10 |
| CaCO$_3$ (tech. grade) | 5 |
| Methyl oleate | 30*** |
| Tap water | q.s. to 1 L | pH adjusted to pH 7.0 with 1N NaOH, sterilized 40 min. at 120° C.
*Peptonized Milk Nutrient, Sheffield Products, Norwich, NY 13815
**Proflo, Traders Protein, Memphis TN 38108
***The amount of methyl oleate was 30 ml The inoculated production medium is incubated in 250-ml or 500-ml Erlenmeyer flasks at 30° C. for 7 to 10 days on a shaker orbiting in a two-inch circle at 260 rpm.

B. Stirred Reactor Fermentation

In order to provide a larger volume of inoculum, 10 ml of incubated first stage medium, prepared as described in Section A, is used to inoculate 400 ml of a second-stage vegetative medium having the same composition as that of the first-stage medium. This second-stage vegetative medium is incubated in a 2-L widemouth Erlenmeyer flask for about 48 hours at 30° C. on a shaker orbiting in a two-inch circle at 260 rpm. Incubated second stage vegetative medium (2 L) thus prepared is used to inoculate 80 to 115 liters of sterile production medium, prepared as described in Section A.

The inoculated production medium is allowed to ferment in a 165-L stirred bioreactor for 7 days to 10 days at a temperature of 30° C. The air-flow and agitator speed in the stirred vessel are computer controlled to maintain a dissolved oxygen level at or above 60% to about 80% of air saturation.

The following tables illustrate the amount of A83543J, A83543L, A83543M, and A83543N that are produced by culture A83543.6.

TABLE X

Amount of formula 2 compounds produced by shake-flask fermentation with culture A83543.6

| Factor | Amount (μg/ml) |
| --- | --- |
| A83543J | 661 |
| A83543L | 133 |
| A83543M | ND* |
| A83543N | ND* |

*Not determined by HPLC assay

TABLE XI

Amount of formula 2 compounds produced by stirred reactor fermentation with culture A83543.6

| Factor | Amount (mg) |
| --- | --- |
| A83543J | 5,282 |
| A83543L | 2,487 |
| A83543M | 136 |
| A83543N | 71 |

EXAMPLE 3

Preparation of A83543J, A83543L, A83543M, and A83543N with Culture A83543.7

The culture *Saccharopolyspora Spinosa* NRRL 18720 may be used as described in Example 2 to prepare the formula 2 compounds. Table XII illustrates the amount of A83543J and A83543L that are produced by shake-flask fermentation of A83543.7.

TABLE XII

Amount of formula 2 compounds produced by shake-flask fermentation with culture A83543.7

| Factor | Amount (μg/ml) |
| --- | --- |
| A83543J | 112 |
| A83543L | 22 |
| A83543M | ND* |
| A83543N | ND* |

*Not determined by HPLC assay

EXAMPLE 4

Isolation of A83543J, A83543L, A83543M, and A83543N

Fermentation broth (105 L), prepared as described in Example 2, was adjusted to pH 10 (initially pH 6.8) by adding 5N NaOH. The resulting mixture was filtered through a ceramic filter. The filtrate was discarded, a mixture of acetone and water (1:1, 50 L) was added to the mycelial solids, and the resulting mixture was filtered. A second mixture of acetone and water (1:1, 50 L) was added to the mycelial solids, and the pH of the resulting mixture was adjusted to pH 3.0 with 25% sulfuric acid. The resulting mixture was filtered, and a third mixture of acetone and water (1:1 50, L) was added to the mycelial solid. The resulting mixture was filtered and the acidic filtrates were combined.

The combined filtrates were extracted with heptane (10 L). The phases were separated and the aqueous phase added to a second portion of heptane (10 L). The pH of the resulting mixture was adjusted to pH 10 with 5N NaOH. The resulting emulsion was diluted with 50 L of water. The phases were separated and the aqueous phase extracted with a third portion of heptane (10 L). The phases were separated and the second and third heptane extracts were combined and concentrated to a volume of about 4 liters. Upon standing, the concentrate separated into 3 phases: aqueous, emulsion, and organic.

The organic phase was lyophilized to give 15.29 g of crude product.

The crude product was dissolved in methanol (500 mL), filtered, and concentrated to dryness in vacuo. The residue was dissolved in a second portion of methanol (20 ml) and applied to a column of LH 20 SEPHADEX (Pharmacia LKB Biotechnology, Inc., Piscataway, N.J., 7.5 cm×46cm), eluting with methanol and collecting 25 ml fractions. Using the HPLC system described in Example 1, the fractions were analyzed to determine which fractions contained the formula 2 compounds. Fractions 18–50 were combined and concentrated to dryness.

The residue was dissolved in a mixture of methanol, acetonitrile, and water (5:5:1) and chromatographed in 1 ml 5 portions on a preparative reverse-phase HPLC column (Rainin DYNAMAX-60A, C18, 41.4 mm×300 mm, 8μm particles, 60Å pore, Woburn, Mass.). The column was eluted with a mixture of methanol, acetonitrile and water (87.5:87.5:25) with ammonium acetate added to a final concentration of 0.1% (pH 7.6). The fractions were analyzed using an HPLC system, similar to that as described in Example 1, combining like fractions and concentrating to give three semi-pure concentrates A, B, and C.

Semi-pure concentrate C was rechromatographed on the system described in the preceding paragraph, loading 200 mL on each of 10 runs. The fractions from each of the runs were combined and concentrated to give preparations C1 and C2. Preparation C2 was chromatographed a third time; however, water was used in place of the 0.1% ammonium acetate (desalting step). Fractions containing A83543L in at least 99.5% HPLC purity were combined and concentrated. The residue was crystallized from ethanol/water (1:1) to give 2.4 g of A83543L. Preparation C1 and semi-pure concentrate B were combined and desalted as described in the preceding paragraph (12×200 mL runs); however, the desired compound was eluted with a mixture of methanol, acetonitrile, and water (11:11:3). The fractions containing A83543J in at least 99.5% HPLC purity were combined and concentrated. The residue was dissolved in hot t-butanol and lyophilized to give 4.3 g of A83543J.

Semi-pure concentrate A was chromatographed as described above, except the desired compounds were eluted with a mixture of methanol, acetonitrile, and water (37.5:37.5:25), with ammonium acetate added to final concentration of 0.1%. The fractions from each of the runs (4) were combined and concentrated to give preparations A1, A2, and A3.

Preparation A1 was chromatographed using the column described above; however, the column was eluted with a mixture of methanol, acetonitrile, and water (2:2:1). Fractions containing A83543M in at least 99.5% HPLC purity were combined and concentrated. The residue was dissolved in t-butanol and lyophilized to give 136 mg of A83543M.

Preparation A2 was chromatographed and processed as described in the preceding paragraph to give 71 mg of A83543N.

EXAMPLE 5

A83543PsaL1

A sample of A83543L (1.0 g) was added to deionized water (90 ml) and a sufficient volume of 1N $H_2SO_4$ (approximately 0.5 ml) was added to cause dissolution. This solution was heated at about 80° C. for 2 hours, and the resulting mixture was allowed to cool to room temperature. The precipitate was collected by filtration, washed with cold deionized water, and dried to give 420 mg of impure A83543PsaL1. The aqueous washes were combined, saturated with NaCl, and extracted with methylene chloride. The combined methylene chloride extracts were washed with brine, dried ($K_2CO_3$), and evaporated to dryness to give 368 mg of a white glass. The residual glass was combined with the precipitate and purified by flash chromatography (silica gel 60, 230-400 mesh), eluting with a mixture of ethyl acetate and hexane (7:3). The fractions containing the desired compound were combined and evaporated to dryness to give 382.8 mg of A83543PsaL1 as a colorless glass.

MS (FD): m/z 590, 591 (M+), 592 (M+H)
IR ($CHCl_3$): 2937, 1715, 1659 $cm^{-1}$
UV (EtOH): $\lambda_{max}$ 242 nm ($\epsilon$10,048)

EXAMPLE 6

Synthesis of A83543M

A83543J (105.4 mg, 0.15 mmol) and sodium acetate trihydrate (144.6 mg, 1.06 mmol) were added to a mixture of methanol and pH 9 buffer solution (Fisher Scientific, Lexington, Mass.). The resulting suspension was heated to about 47° C., and then iodine (46.6 mg, 0.18 mol) was added in one portion. After approximately 10 min., the solution became homogeneous. After four hours at 47° C., the reaction was added to a 5% sodium thiosulfate solution. The resulting colorless aqueous mixture was extracted with methylene chloride. The methylene chloride extracts were combined, washed with brine, and dried over $K_2CO_3$. The dried methylene chloride solution was evaporated to dryness in vacuo to give 57.3 mg of A83543M as a pale yellow glass (54% yield).

EXAMPLE 7

Synthesis of A83543N

Using a procedure similar to that described in Example 6, A83543L (102.5 mg) was chemically converted to A83543N (66.5 mg).

EXAMPLE 8

The following formulations are typical of the insecticidal compositions useful in this invention.

| A. Aqueous Suspension | |
|---|---|
| A83543L | 12.5% |
| TERGITOL TMN-6 (nonionic surfactant) | 1.0% |
| ZIOSYL 200 (silica) | 1.0% |
| AF-100 (silicon based antifoam agent) | 0.2% |
| Xanthan solution (2%) | 10.0% |
| MAKON 10 (10 moles ethyleneoxide nonylphenol surfactant) | 9.0% |
| Tap Water | 66.3% |
| B. Emulsifiable Concentrate | |
| A83543M | 12.4% |
| EXXON 200 (naphthalene solvent) | 83.6% |
| TOXIMUL H (nonionic/anionic surfactant blend) | 2.0% |
| TOXIMUL D (nonionic/anionic surfactant blend) | 2.0% |

EXAMPLE 9

The following exemplary compositions illustrate the sort of formulations used to practice the method of the present invention.

| A. Feed Premix | |
|---|---|
| A83543L | 10% |
| Rice hulls | 85 |
| Light mineral oil | 5 |
| B. Feed Premix | |
| A83543M | 25% |
| Alfalfa meal | 60 |
| Powdered clay | 5 |
| Molasses | 10 |
| C. Suspension | |
| A83543N | 30% |
| Naphthalenesulfonate salt | 5 |
| Nonionic surfactant | 5 |
| Fumed silica | 1 |
| Water | 59 |
| D. Drip-On Solution | |
| A83543L | 20% |
| Nonionic surfactant | 0.8 |
| Propylene glycol | 15 |
| Water | 64.2 |
| E. Drip-On Suspension | |
| A83543M | 10 |
| Nonionic surfactant | 1 |
| Light mineral oil | 89 |
| F. Injectable Solution | |
| A83543N | 15% |
| Propylene glycol | 85 |
| G. Injectable Suspension | |
| A83543L | 25% |
| Propylene glycol | 15 |
| Water | 60 |
| H. Injectable Suspension | |
| A83543M | 30% |
| Polyvinylpyrrolidone | 2 |
| Water | 68 |

We claim:

1. A process for preparing a compound of formula 2

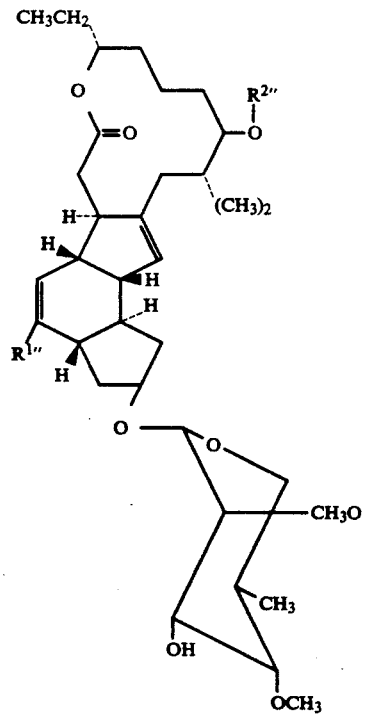

wherein
$R^{1''}$ is hydrogen or methyl; and $R^{2''}$ is a group of formula

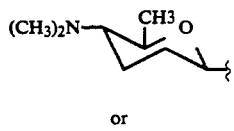

or

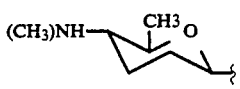

which comprises culturing, in a suitable culture medium under submerged aerobic fermentation conditions until a recoverable amount of a compound of formula 2 is produced, an A83543J-producing strain of *Saccharopolyspora spinosa* derived from mutants of culture NRRL 18395 and recovering a compound of formula 2 from the culture medium.

2. A process of claim 1 further comprising the step of recovering the following compound:

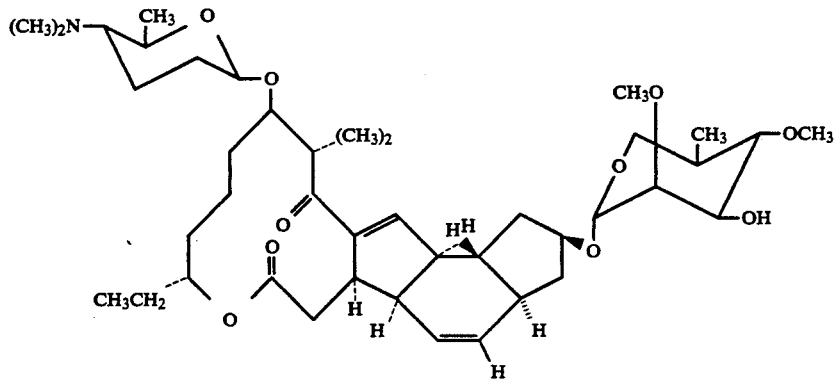

3. A process of claim 1 further comprising the step of recovering the following compound:

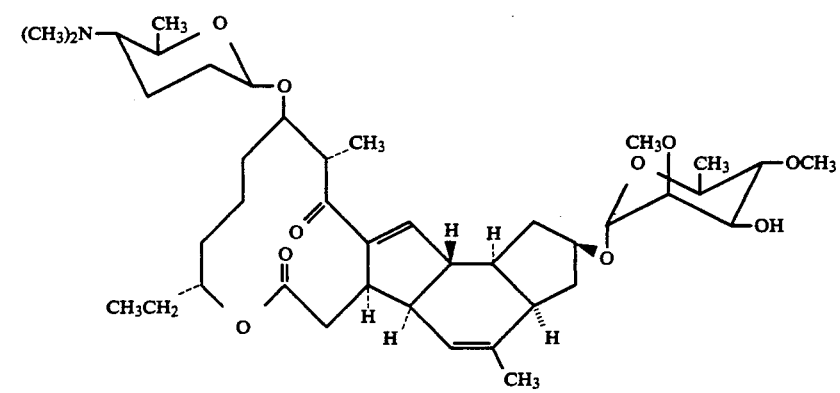

4. A process of claim 1 further comprising the step of recovering the following compound:

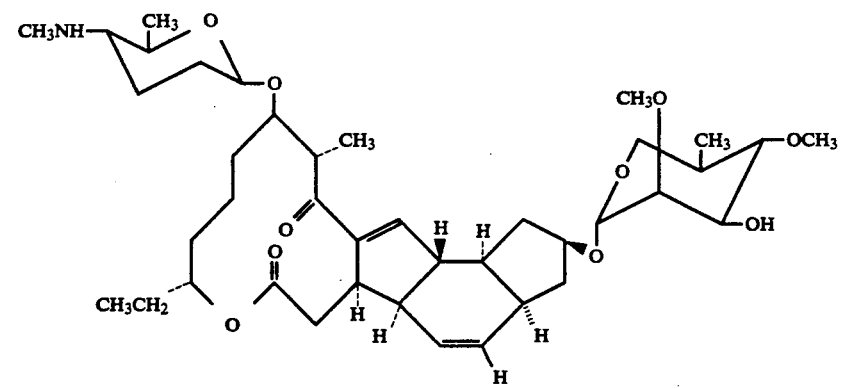

5. A process of claim 1 further comprising the step of recovering the following compound:

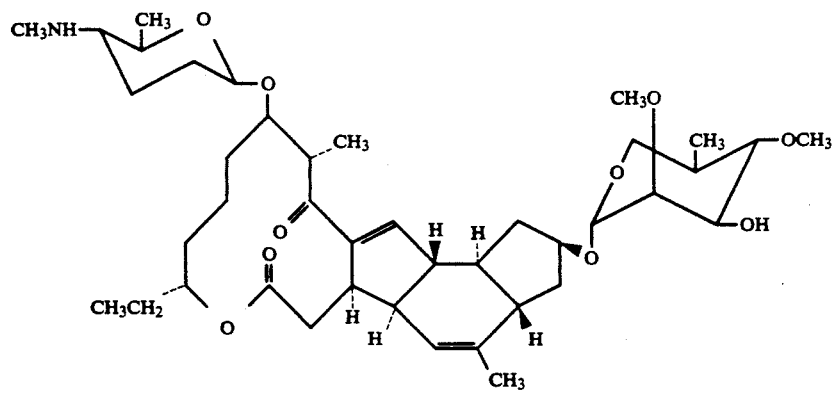
6. A process of claim 1 wherein the A83543J-producing strain of *Saccharopolyspora spinosa* is NRRL 18719, or an A83543J-producing mutant thereof.
7. A process of claim 1 wherein the A83543J-producing strain of *Saccharopolyspora spinosa* is NRRL 18720, or an A83543J-producing mutant thereof.
* * * * *